United States Patent [19]

Sairenji

[11] Patent Number: 4,639,221
[45] Date of Patent: Jan. 27, 1987

[54] TOOTH CLAMP

[76] Inventor: Michihiko Sairenji, 14-9, Hatanodai 3-chome, Shinagawa-ku, Tokyo, Japan

[21] Appl. No.: 769,736

[22] Filed: Aug. 27, 1985

[30] Foreign Application Priority Data

Dec. 18, 1984 [JP] Japan .......................... 59-191818[U]

[51] Int. Cl.$^4$ ............................................. A61C 5/12
[52] U.S. Cl. .................................................. 433/139
[58] Field of Search ........................................ 433/139

[56] References Cited

U.S. PATENT DOCUMENTS 803,045 10/1905 Babcock ............................. 433/139
4,265,623 5/1981 Soelberg et al. .................... 433/139

Primary Examiner—Robert Peshock
Attorney, Agent, or Firm—Cushman, Darby & Cushman

[57] ABSTRACT

A tooth clamp for use on a tooth includes a pair of gripping plates interconnected by a resilient arcuate bridge, a stopper mount on at least one of the gripper plates, and a stopper mounted on the stopper mount and having a portion for engagement with the tooth. The gripping plates are prevented by the stopper from moving toward the roots of the tooth into biting engagement with the gum surrounding the tooth. The tooth or its root canal can therefore be treated safely and quickly. The stopper is adjustably supported on the stopper mount so that the height of the gripping plates with respect to the top of the tooth can be adjusted dependent on the height of the tooth.

5 Claims, 2 Drawing Figures

TOOTH CLAMP

BACKGROUND OF THE INVENTION

1. Field of the Invention

The present invention relates to a tooth clamp, and more particularly to a tooth clamp for use with a rubber dam upon treatment of the root canal of a tooth.

2. Description of the Prior Art

When treating the root canal of a tooth as by extracting an exposed nerve in the central cavity formed in a decayed molar tooth or remedying such a decayed molar tooth, it is known to use a rubber dam sheet in surrounding relation to the decayed tooth for preventing a medicine from entering the oral cavity.

FIGS. 3 and 4 of the accompanying drawings illustrate a conventional process of using such a rubber dam sheet. The rubber dam sheet 11 has a central hole 11a smaller than the outer profile of a decayed tooth 12 to be treated. A clamp 13 has a pair of gripping plates 14, 14 having respective arcuate tooth contacts or grippers 14a, 14a defining a tooth gripping space P', the gripping plates 14, 14 also having spreading holes 14b, 14b respectively. The clamp 13 also includes a resilient arcuate bridge 15 interconnecting the gripping plates 14, 14. When attaching the rubber dam sheet 11 and the clamp 13 to the decayed tooth 12, the gripping plates 14, 14 are placed over the rubber dam sheet 11 so that the tooth gripping space P' is in vertical registry with the hole 11a in the rubber dam sheet 11. Then, the pointed tip ends of rubber dam forceps (not shown) are inserted respectively in the spreading holes 14b, 14b. While spreading the gripping plates 14, 14 apart with the rubber dam forceps to enlarge the tooth gripping space P' against the resiliency of the arcuate bridge 15, the rubber dam sheet 11 and the gripping plates 14, 14 are fitted over the tooth 12 in surrounding relation thereto. By spreading the gripping plates 14, 14 with the rubber dam forceps to enlarge the tooth gripping space P', the hole 11a in the rubber dam sheet 11 is also enlarged. After the rubber dam sheet 11 and the clamp 13 have been mounted on the tooth 12, the rubber dam forceps are removed to allow the hole 11a to shrink into intimately fitting relation to the cirfumerential surface of the neck of the decayed tooth 12.

Then, the outer periphery of the rubber sheet 11 is kept taut by a rubber dam holder 16. The clamp 13 serves as a tool for preventing the rubber dam sheet 11 from being detached from the tooth 12.

Since the decayed tooth 12 is surrounded by the rubber dam sheet 11, any medicine applied to the tooth 12 is prevented by the rubber dam sheet 11 from flowing into the oral cavity. Therefore, the decayed tooth 12 can quickly be treated while protecting the patient from the danger of the medicine.

However, since the tooth 12 is progressively tapered toward its roots, the clamp 13 tends to move down toward the tooth roots under the resiliency of the bridge 15 and due to contact by the dentist's fingers during treatment. Therefore, the edges of the tooth grippers 14a, 14a are caused to bite into the gum 17.

SUMMARY OF THE INVENTION

In view of the problem of the conventional tooth clamp, it is an object of the present invention to provide a tooth clamp which is prevented from being lowered toward the roots of a tooth clamped by the tooth clamp and which can be adjusted in position with respect to the tooth.

According to the present invention, there is provided a tooth clamp for use on a tooth including a pair of gripping plates interconnected by a resilient arcuate bridge, a stopper mount on at least one of the gripper plates, and a stopper mounted on the stopper mount and having a portion for engagement with the tooth.

The gripping plates are prevented by the stopper from moving toward the roots of the tooth into biting engagement with the gum surrounding the tooth. The tooth or its root canal can therefore be treated safely and quickly.

The stopper is adjustably supported on the stopper mount so that the height of the gripping plates with respect to the top of the tooth can be adjusted dependent on the height of the tooth.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
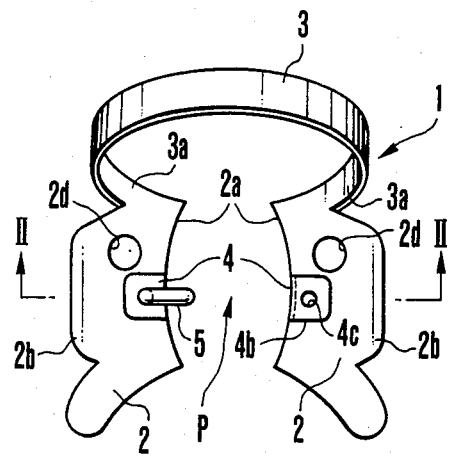
FIG. 1 is a plan view of a tooth clamp according to the present invention.
Figure 2:
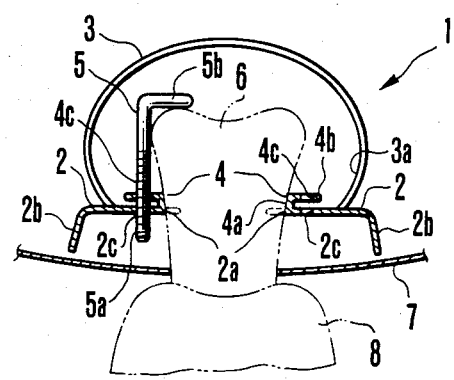
FIG. 2 is a cross-sectional view taken along line II—II of FIG. 1.
Figure 3:
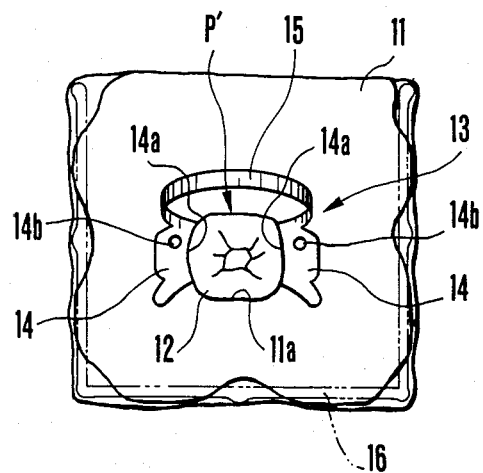
FIG. 3 is a plan view of a conventional tooth clamp as mounted on a tooth.
Figure 4:
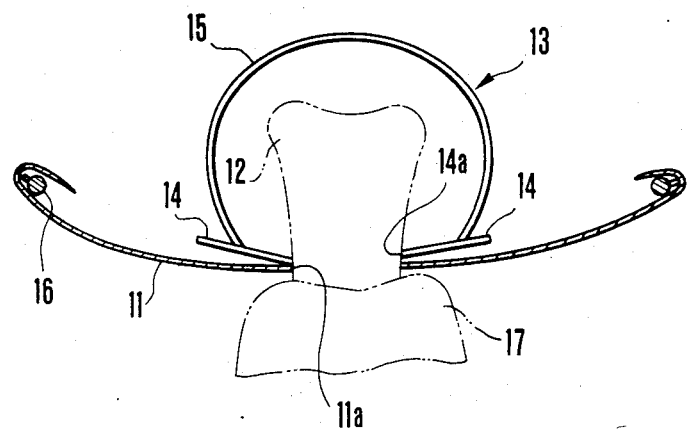
FIG. 4 is an enlarged side elevational view of the tooth clamp shown in FIG. 3.

FIGS. 1 and 2 show a tooth clamp according to the present invention.

The tooth clamp 1 is composed of a pair of gripping plates 2, 2 integrally joined by a resilient arcuate bridge 3.

The gripping plates 2, 2 have arcuate tooth contacts or grippers 2a, 2a, respectively, comprising longitudinal concave side edges confronting each other. The gripping plates 2, 2 also have opposite side edges bent downwardly as wings 2b, 2b, respectively.

Each of the gripping plates 2, 2 has a stopper mount 4 positioned adjacent to one of the arcuate tooth grippers 2a, 2a and composed of an upstanding wall 4a and a horizontal plate 4b extending therefrom. The horizontal plate 4b has a threaded hole 4c defined therein. Each gripping plates 2, 2 also has a threaded hole 2c defined therein directly below the threaded hole 4c.

A stopper 5 in the form of a rod has an externally threaded portion 5a on the lower end of a straight portion of the rod. The externally threaded portion 5a is threaded in the threaded holes 4c, 2c of one of the gripping plates 2, 2. The stopper 5 also has a bent engaging end 5b extending perpendicularly to the straight rod portion thereof.

The confronting arcuate tooth grippers 2a, 2a define a tooth gripping space P therebetween which has a width slightly smaller than the narrowest portion of the tooth 6. The resilient arcuate bridge 3 has opposite ends 3a, 3a joined to opposite longitudinal ends of the gripping plates 2, 2, respectively, the opposite ends 3a, 3a being directed downwardly. The gripping plates 2, 2 have respective holes 2d, 2d for inserting therein the tip ends of rubber dam forceps used to spreading the tooth gripping surface P. The tooth clamp 1 is used with a rubber dam sheet 7 on the tooth 6 which is surrounded at its lower portion by a gum 8.

Since the stopper 5 has the externally threaded portion 5a on the lower end thereof, the height of the engaging end 5b of the stopper 5 with respect to the tooth 6 can freely be adjusted simply by turning the externally threaded portion 5a. When the clamp 1 is used, the engaging end 5b is held in engagement with the top of the tooth 6, as shown in FIG. 2, so that the height of the gripping plates 2, 2 from the top of the tooth 6 can be adjusted dependent on the height of the tooth 6 to be treated.

Therefore, the gripping plates 2, 2 are prevented from being lowered into biting engagement with the gum 8. The tooth 6 can be treated safely and quickly.

The stopper mounts 4, 4 are disposed respectively on the gripping plates 2, 2. The single stopper 5 can be mounted on one of the stopper mounts 4, 4 so that it will not interfere with the treatment of the tooth 6. The stopper 5 may be fixedly attached to one of the stopper mounts 4,4 above the rubber dam sheet 7.

Although a certain preferred embodiment has been shown and described, it should be understood that many changes and modifications may be made therein without departing from the scope of the appended claims.

What is claimed is:

1. A tooth clamp for use on a tooth surrounded by a gum and having a given height and a top comprising:

(a) a resilient arcuate bridge;
   (b) a plurality of gripping plates interconnected by said resilient arcuate bridge;
   (c) a mount positioned on at least one of said gripping plates; and
   (d) a stopper means, mounted on said mount, for engaging with the tooth along a predetermined extent of the given height of the tooth to prevent said gripping plates from moving into biting engagement with said gum and having means for adjusting a point of engagement along said given height of the tooth.

2. A tooth clamp according to claim 1, wherein said gripping plates have respective tooth grippers along longitudinal edges thereof, said mount being positioned adjacent to one of said tooth grippers and having an upstanding wall and a horizontal plate extending therefrom, said horizontal plate being supported on said upstanding wall.

3. A tooth clamp according to claim 2, wherein said horizontal plate has a first threaded hole defined therein, and said at least one gripping plate has a second threaded hole defined therein in registry with said first threaded hole, said stopper means including a rod having on one end thereof a means for threading in said first and second threaded holes.

4. A tooth clamp according to claim 3, wherein said rod includes a bent engaging portion on another end thereof for engagement with the top of the tooth.

5. A tooth clamp according to claim 1, wherein said mount is disposed on each of said gripping plates.

* * * * *